United States Patent [19]

O'Hanlon et al.

[11] 4,222,942

[45] Sep. 16, 1980

[54] ISOLATION OF ORGANIC ACIDS

[75] Inventors: Peter J. O'Hanlon, Redhill; Maurice C. Woodford, Billingshurst; Norman H. Rogers, Rudgwick, all of England

[73] Assignee: Beecham Group Limited, England

[21] Appl. No.: 946,873

[22] Filed: Sep. 29, 1978

[30] Foreign Application Priority Data

Sep. 30, 1977 [GB] United Kingdom ............... 40678/77

[51] Int. Cl.$^2$ ............................................. C07D 309/06
[52] U.S. Cl. ............................................. 260/345.8 R
[58] Field of Search ................................. 260/345.8 R

[56] References Cited

U.S. PATENT DOCUMENTS 4,139,629  2/1979  Rogers ........................ 260/345.8 R

FOREIGN PATENT DOCUMENTS 1395907  5/1975  United Kingdom ............. 260/345.8 R

*Primary Examiner*—Nicky Chan
*Attorney, Agent, or Firm*—Jacobs & Jacobs

[57] ABSTRACT

A process for the purification of pseudomonic acid, particularly suitable for isolating the compound when prepared by bacterial culture, comprises making a solution in an organic solvent of the acidic components of the crude preparation substantially free of the neutral components. The polarity of the organic solvent is adjusted so that the pseudomonic acid crystallizes. This may be achieved either by adding a non-polar diluent such as n-heptane to the solution for example in methyl iso-butyl ketone; or by employing a di-$C_{1-6}$ alkyl ether in which the acidic components dissolve and then crystallize out.

9 Claims, No Drawings

ISOLATION OF ORGANIC ACIDS

This invention relates to a method for preparing pseudomonic acid.

Pseudomonic acid is a compound of Formula (I):

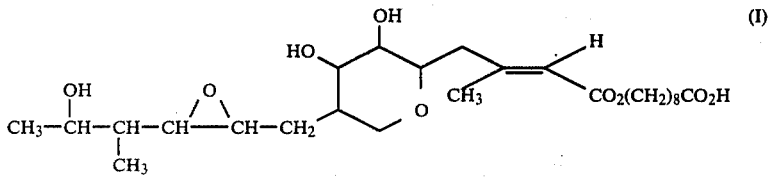

The compound has antibacterial activity and is therefore of value in the treatment of bacterial infections in man and animals, particularly infections of the upper respiratory tract.

This compound together with a method for its preparation is disclosed in British Pat. No. 1,395,907. The method disclosed in British Pat. No. 1,395,907 for the preparation of pseudomonic acid consists essentially of isolating a mixture containing the principle active acid components from a culture medium on or in which *Pseudomonas fluorescens* has been grown under aerobic conditions and thereafter separating the acid from the mixture by chromatography.

The present invention provides a process for isolating pseudomonic acid from a crude preparation thereof which process comprises making a solution in a water immiscible organic solvent of the acidic components of the crude preparation substantially free of any neutral components, the water immiscible organic solvent being of a polarity such that the pseudomonic acid will preferentially crystallise from the solution, allowing the pseudomonic acid to crystallise, and thereafter recovering the crystals.

The method of this invention is particularly suitable for purifying crude pseudomonic acid preparations obtained by isolating the anti bacterially active acidic components from culture media on or in which pseudomonic acid producing strains of bacteria have been grown, but the method is also applicable to preparing pseudomonic acid from crude preparations prepared by chemical synthesis.

Where the invention is employed to isolate pseudomonic acid from culture media the process is most suitable carried out as follows. A pseudomonic acid producing bacterium, in general a strain of bacterium of the family Pseudomonas is cultured by a standard method under aerobic conditions in or on a suitable culture medium. Such culture media are generally known, and contain inorganic salts and sources of assimilable nitrogen and carbon. Most suitably the bacterium used is *Pseudomonas fluorescens*. One suitable strain publicly available is *Pseudomonas fluorescens* NCIB 10586. The micro-organism is allowed to grow until a suitable quantity of pseudomonic acid is present in the culture medium. Solid particles are then removed from the medium by filtration or centrifugation to produce a clear liquor. The pH of the clear liquor is adjusted to pH 4.0–5.0, pH 4.5 being optimal, and then extracting with water immiscible organic solvent for the active components.

Suitable solvents may be found by trial and error, but we have found iso-butylmethyl ketone (MIBK) to be satisfactory. Other sovents include halogenated hydrocarbons esters and ether containing 5% ethanol.

The acidic components are then extracted into an aqueous phase which has a pH in the range 7 to 9, pH 8.5 being optimal, the neutral contaminants remaining in the organic phase. The aqueous extract is then acidified to a pH in the range 4.0–5.0, pH 4.5. being optimal, and extracted into a water immiscible polar organic solvent, thereby producing the extract of the principal acidic components in a polar organic solvent, free of any neutral components. Suitable polar water immiscible organic solvents include for example the alkyl esters of alkanoic acids, for example $C_1$ to $C_6$ alkyl $C_1$ to $C_6$ alkanoates methyl and ethyl $C_6$ to $C_{10}$ alkanoates $C_6$ to $C_{10}$ alkylacetates, water immiscible ketones such as $C_6$ to $C_{10}$ alkanones such as MIBK, water immiscible alcohols such as the $C_5$ to $C_{10}$ alkanols and halogenated hydrocarbons such as chloroform, methylene chloride and ethylene chloride.

The solution may then optionally be washed with water. It is preferable that the solution should be dried. Drying with the aid of common agents such as calcium chloride, sodium sulphate or magnesium sulphate is sufficient.

The polarity of the solution is then reduced by adding a non-polar diluent which causes the pseudomonic to crystallise.

Accordingly one embodiment of the invention provides a process for isolating pseudomonic acid from a crude preparation thereof, which process comprises making a solution of the acidic components of the crude preparation, substantially free of any neutral components, in a polar water immiscible organic solvent, and adding a non-polar diluent which is miscible with the organic solvent, to the solution in order to allow pseudomonic acid to crystallise and thereafter recovering the crystals.

Suitable polar solvents have been discussed above.

Suitable non-polar diluents include the alkanes, toluene, benzene and di-$C_1$ to $C_6$ alkyl ethers. Most convenient are those short chain alkanes which are liquid at room temperature (ca 20° C.), for example $C_5$–$C_{12}$ alkanes, suitably $C_5$–$C_9$ alkanes. A preferred non-polar diluent is n-heptane.

It is preferred that the diluted solution should be left to stand for some time before the solid is recovered, and crystallisation may be encouraged by adding a previously obtained seed crystal of pseudomonic acid.

The temperature at which the dilution and crystallisation is carried out is not critical, but we have found room temperature to be most convenient. It is however useful to cool the diluted solution to ensure complete crystallisation.

Alternatively it is possible to carry out the process of this invention by preparing a solution of the acidic components of a crude pseudomonic acid preparation in a water immiscible organic liquid of a polarity such that pseudomonic acid will preferentially crystallise without the necessity of adding a non-polar diluent to reduce the polarity. Suitable for this purpose are the di-$C_1$ to $C_6$ alkyl ethers, in particular diethyl ether.

Accordingly in a further embodiment, the invention provides a process for isolation pseudomonic acid from a crude preparation thereof, which process comprises making a solution of the acidic components of the crude preparation, substantially free of any neutral components, in a di-$C_1$-$C_6$ alkyl ether, allowing pseudomonic acid to crystallise from the solution and recovering the crystals.

Where this embodiment of the invention is used to isolate pseudomonic acid from culture media, it is most convenient to first prepare a solution of acid components in a polar organic solvent as described above and then remove the solvent, yielding a residue which may then be dissolved in the chosen ether, and allowed to crystallise.

The crystallisation is preferably effected from a dry solution. This is generally achieved by drying the solution of the acidic components as described above before removing the solvent. We have found that it is sufficient to dry the solution over common drying agents such as magnesium sulphate or sodium sulphate, but better results are obtained when a more powerful drying agent such as a molecular sieve is employed, and/or when a solvent such as MIBK is employed which forms an azeotrope with any residual water thereby effecting additional drying as the solvent is evaporated. It is sufficient to dry the ether over for example magnesium or sodium sulphate, but better results are obtained with sodium dried ether.

The temperature at which the crystallisation takes place is not critical, but we have found room temperature to be convenient. It is useful to cool the solution to ensure complete crystallisation. Again it is preferable to seed the solution by adding a crystal of pseudomonic acid to the solution.

The process of the invention is most successful when used with crude preparations containing substantial proportions of pseudomonic acid. When the crude preparation contains small amounts of the desired compound the process may have to be repeated a number of times.

For use as an antibacterial agent pseudomonic acid prepared by this process may be formulated in accordance with standard veterinary and pharmaceutical procedure. Such compositions form a further aspect of the invention.

The following examples illustrate the process of this invention.

EXAMPLE 1

Culture medium (1500 l) containing pseudomonic acid (408 g) was partially clarified on a rotary precoat filter and further clarified by centrifugation giving clarified liquor (1285 l) containing pseudomonic acid (372 g). This was acidified to pH 4.5 using 50% hydrochloric acid and was extracted with MIBK (300 l) by metering the liquor at 8 l min$^{-1}$ and solvent at 2 l min$^{-1}$ into an in-line static mixer.

The two immiscible phases were separated by centrifugation. The solvent extract containing pseudomonic acid (226 g) was extracted with 2% w/v sodium bicarbonate solution (60 l) pre-adjusted to pH 8.5. The phases were separated by centrifugation. MIBK (12 l) was added to the aqueous extract and the aqueous phase was acidified to pH 4.5 using 50% hydrochloric acid. The organic phase was separated and washed with deionised water (6 l), the solution was concentrated to 1.5 l dried with magnesium sulphate. The magnesium sulphate was removed by filtration and the n-heptane (750 ml) added to the dry solution. The mixture so produced was left to stand at 5° C. for 12 hours. The product was filtered and washed with 50:50 MIBK heptane (1 l) and then with heptane (1 l) and dried in vacuo at 25°. Yield 125 g. Purity 92–93%. λmax (EtOH) 222 nm (Emax 14,500). γmax (KBr) 3470, 1728, 1720 1712, 1650 cm$^{-1}$. $\delta_H$ (d$_6$-DMSO) 5.61 (1H,s, C$\underline{H}$=C), 2.06 (3H,s, $$\begin{array}{c} C=C)), \\ | \\ C\underline{H}_3 \end{array}$$

1.04 (3H,d,J=6.5 Hz, >CHC$\underline{H}_3$), 0.80 (3H,d,J=6.5 Hz, >CHC$\underline{H}_3$). $\delta_C$ (d$_6$-DMSO) 174.3, 165.7, 116.6, 74.5, 69.4, 68.2, 67.7, 64.6, 62.9, 59.0, 54.6, 42.5, 41.8, 40.0, 33.6, 31.5, 28.5, 28.1, 25.4, 24.4, 20.0, 18.5, 11.6.

EXAMPLE 2

A solvent extract prepared as in Example 1 containing pseudomonic acid (226 g) was extracted with 2% w/v sodium bicarbonate solution (60 l) pre-adjusted to pH 8.5. The phases were separated by centrifugation. A portion of the sodium bicarbonate solution (12 l) was washed with MIBK (3 l) and the MIBK discarded. MIBK (3 l) was added to the aqueous extract and the aqueous phase was acidified to pH 4.5 using 50% hydrochloric acid. The organic phase was separated and washed with deionised water (3×3 l) the organic phase was then separated and dried with magnesium sulphate. The magnesium sulphate was removed by filtration and the solvent was evaporated in vacuo to an oil. Sodium dried diethyl ether (800 ml) was added to the oil, the mixture was stirred and the solution was decanted from the small quantity of insoluble residue. The solution was seeded with a crystal of pure acid and stirred at room temperature for two hours, then stored in a cold room (5° C.) overnight. The solid which deposited was collected by filtration, washed with dry ether (100 ml) and dried in vacuo. Yield 38.4 g. M.p. 77°–78° C. [α]$_D^{20}$ −19.3(c=1 MeOH) $C_{26}H_{44}O_9$ requires C, 62.38; H, 8.86; found C, 62.62; H, 8.70%.

What is claimed is:

1. Process for the isolation of pseudomonic acid from a crude preparation thereof which comprises extracting a solution of said crude preparation in a water immiscible organic solvent with an aqueous media having a pH value of 7 to 9 so as to obtain an aqueous solution of the acidic components of the crude preparation substantially free of any neutral components, lowering the pH of said aqueous solution to a value of from 4.0 to 5.0, and extracting the pH adjusted aqueous solution either (a) with a polar water immiscible organic solvent and thereafter adding a diluent which is sufficiently nonpolar to reduce the polarity of, but is miscible with, said polar organic solvent so as to effect crystallization of said pseudomonic acid or (b) with a dialkyl ether wherein each alkyl has 1 to 6 carbon atoms and allowing said pseudomonic acid to crystallize therefrom; and thereafter isolating said pseudomonic acid.

2. A process according to claim 1 wherein the crude preparation is a culture medium in which pseudomonic acid has been produced from a bacterium.

3. Process according to claim 1 wherein said pH adjusted aqueous solution is extracted with a polar water immiscible organic solvent and a diluent is thereafter added.

4. Process according to claim 3 wherein the polar water immiscible organic solvent is methyl isobutyl ketone.

5. Process according to claim 3 wherein the diluent is an alkane of 5 to 9 carbon atoms.

6. Process according to claim 5 wherein the alkane is n-heptane.

7. Process according to claim 1 wherein said pH adjusted aqueous solution is extracted with a dialkyl ether.

8. Process according to claim 7 wherein crystallization is effected by seeding with crystalline pseudomonic acid.

9. Process according to claim 7 wherein the dialkyl ether is diethyl ether.

* * * * *